United States Patent [19]

Lin et al.

[11] Patent Number: 4,906,101

[45] Date of Patent: Mar. 6, 1990

[54] TURBIDITY MEASURING DEVICE AND METHOD

[75] Inventors: Ellen Y. Lin; James Teng, both of St. Louis, Mo.

[73] Assignee: Anheuser-Busch Companies, Inc., St. Louis, Mo.

[21] Appl. No.: 125,807

[22] Filed: Nov. 24, 1987

Related U.S. Application Data

[63] Continuation of Ser. No. 846,797, Apr. 1, 1986, abandoned, which is a continuation of Ser. No. 670,262, Nov. 13, 1984, abandoned, which is a continuation-in-part of Ser. No. 502,135, Jun. 8, 1983, abandoned.

[51] Int. Cl.$^4$ ............................................. G01N 21/00
[52] U.S. Cl. ...................................... 356/442; 356/36; 435/291
[58] Field of Search ................... 356/442, 36; 435/291

[56] References Cited

U.S. PATENT DOCUMENTS

| | | | |
|---|---|---|---|
| 3,962,041 | 6/1976 | Muller | 435/291 |
| 4,027,971 | 6/1977 | Kolman | 356/36 |
| 4,072,424 | 2/1978 | McMullan | 356/442 |

Primary Examiner—Bernard Pianalto
Attorney, Agent, or Firm—Gravely, Lieder & Woodruff

[57] ABSTRACT

This disclosure relates to a device for measuring turbidity in static or dynamic streams wherein the fluid has up to 8500 ppm solids and at depth of up to 8″. The device contains a high intensity light source, means for controlling the wavelength of the transmitted light to between 550–900 nm to filter out color variables in the streams, and a very sensitive photosensor aligned with the viewing means for picking up the light transmitted through the streams.

17 Claims, 2 Drawing Sheets

TURBIDITY MEASURING DEVICE AND METHOD

This is a continuation of co-pending application Ser. No. 846,797 filed on Apr. 1, 1986, now abandoned, which is a continuation of Ser. No. 670,262 filed Nov. 13, 1984 (now abandoned) which is a continuation-in-part of Ser. No. 502,135 filed June 8, 1983 (now abandoned).

BACKGROUND OF THE INVENTION

This invention relates to the measurement of turbidity in static and dynamic situations and in particular relationship to beer production concerns a device for static and dynamic measurement of the turbidity of beer flowing through a pipe line.

In beer production, it is necessary both to chill-proof and to filter the beer for better sales appeal, good flavor and long shelf life. Both operations require careful monitoring of the beer turbidity. In the case of chill-proofing, turbidity indicates the extent of sedimentation induced by the chill-proofing agent. The proper separation of clear beer from the sediments affects directly the beer recovery rate and operation time. In the case of filtration, turbidity suggests the required filter aid feed rate which influences the filter operation efficiency and the clarity of the finished beer.

There are presently available commercially several turbidity measurement devices. However, they are not satisfactory for beer production. These devices all give erratic readings unless used in narrow turbidity ranges. In beer production the turbidity measuring devices must give reproducible readings over a broad turbidity range of 0–8500 ppm.

Presently available devices also are usable only within a limited range of fluid depths where they give accurate and reproducible measurements. These devices usually are limited to about a 2″ deep cell. In beer production, however, pipe lines have inside diameters ranging up to about 8″ and the need is for a turbidity measuring device which will read accurately across such depths of fluid.

Further criteria for turbidity measurements in beer production is that the turbidity measuring device needs to have the capability to measure various types of beer that have different colors and various concentrations of ingredients.

Accordingly, it is a principal object of this invention to provide a turbidity measuring device which is suitable for use in beer production in both the chill-proofing and filtering steps. It is a further object of this invention to provide a turbidity measuring device which gives consistently reproducible results in a dynamic situation over a broad turbidity range and across pipe lines of up to 8″ in diameter. These and other objects and advantages will become apparent hereinafter.

The present invention comprises a device and process for measuring turbidity of beer in a static and dynamic situation over a broad range of turbidity (0–8500 ppm) and through a pipe line of up to 8″ in diameter.

This invention also is applicable to any instance where measurement of suspended solids is needed. However, for illustrative purposes, the device and process is described in this application in relation to a beer producing process.

DETAILED DESCRIPTION

Figure 1:
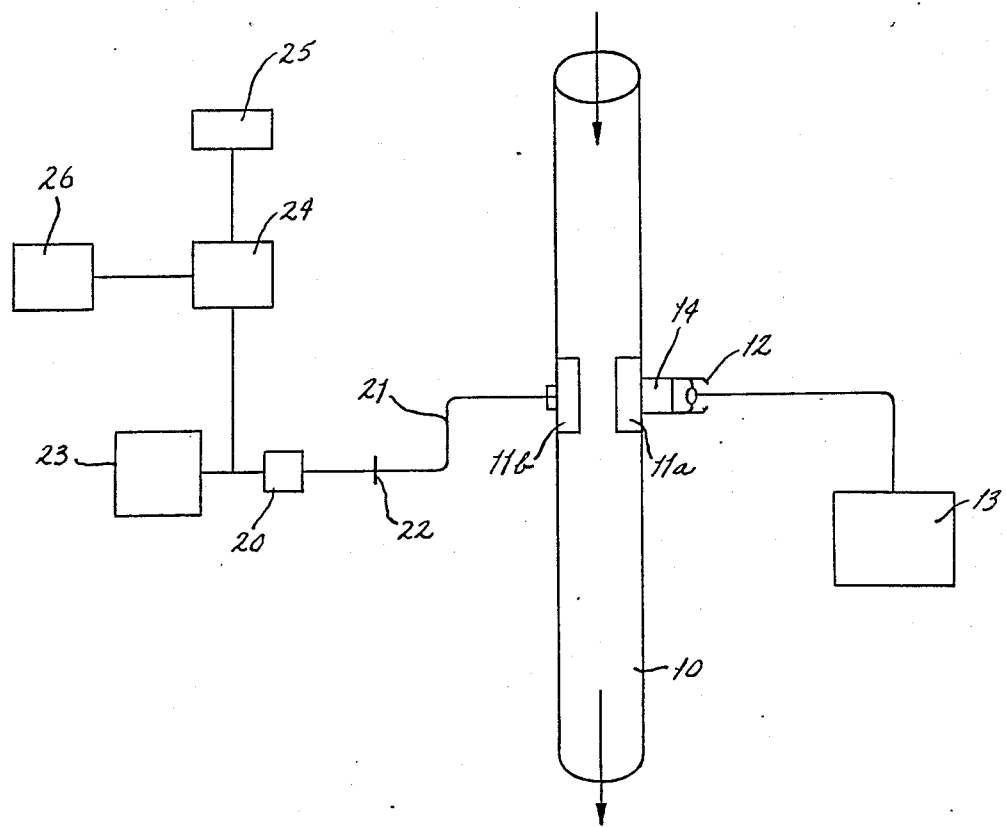
FIG. 1 shows an example of the schematic arrangement of the components for measuring the turbidity of beer in a pipe line.

In order to be commercially acceptable, a beer must possess certain properties; for example, it must be sparkling clear. An additional property which is most significant to beer connoisseurs is referred to as chill stability. This relates to the property noted above as "sparkling clear". As the name implies, on occasion a haze forms in some beer when it is chilled. As the temperature of the beer is returned to room temperature, the haze usually disappears, only to reappear upon subsequent rechilling. This haze is referred to as chill haze.

Several methods are used in the brewing industry for chill-proofing of beer, the method of choice depending on the process economics and on the flavor characteristics desired in the end product.

One of the methods widely used in the trade for chill-proofing of beer is based on the precipitation and removal of proteinacious constituents from beer using a solution of plant tannin. Other methods of precipitation include bentonite, silica gel and polyvinyl polypyrrolidone. In any event, the measurement of turbidity is important in separating the clear beer from the sediments. The faster and quicker this can be done, the greater is the production of beer from a particular plant.

The final stage of clarification of beer is the filtration of the clear beer decanted off the sediment or sludge from the sedimentation. This requires the use of a filter and filter aid, such as diatomaceous earth. The turbidity of the beer determines the amount of the filter aid to add to the system. Also the greater the amount of filter aid that needs to be added, the shorter the life cycle of the filter. This increases cost and slows down beer production from the plant.

The drawing shows a schematic representation of the apparatus for measuring turbidity which is the subject of this application.

The principal and essential components for the turbidity measuring device are a light source to provide a suitable high intensity light beam either of a precise preselected wavelength range or in combination with filter means to permit passage of light of only said preselected wavelength range, a very sensitive light detector, and an amplifier and signal display to allow readout of the transmitted light. A light transmitter may be incorporated into the system to transmit the light that passes through the fluid to the light detector.

In FIG. 1, the numeral 10 denotes a pipe line which can be from about 2″ to about 8″ in diameter as used in a conventional brewery. The line 10 usually is stainless steel and positioned in the line 10 is a glass window 11a–b which allows viewing of the contents of the line 10. The window 11a–b has opposed sections 11a and 11b to allow light to pass through the line 10 and through its contents in a straight line. A light source 12 is positioned in alignment with the window 11a–b and is operated by a power supply, including a stabilizer 13. The light source 12 is a quartz halogen lamp or any light source which generates a single or a band of wavelengths in the range of 550–900 nm and a suitable commercially available item is a Phillips PCS 150 lamp distributed by GMI Photographic, Inc. of Farmingdale, N.Y. The use of the stabilizer and power supply insures a steady source of constant voltage to the lamp 12 whereby a steady stream of light of constant wavelength is emitted and passed through the window 11a. A suitable product is a Phillips PCS 150 lamp Control. Another method to correct the light intensity change due to power source fluctuation is to use an internal standard, such as the original light, instead of a power stabilizer.

Interposed between the lamp 12 and the window 11a are light filters 14. The filters 14 are dichroic filters of wavelengths of about 550 to about 900 nm. The purpose of the filters is to minimize the color effect of the beer from the output so that only turbidity affects the light passing through the window 11a–b. These filters can be eliminated if a light source which generates a single wavelength or a band of wavelengths between 550 to 900 nm is used.

On the opposite side of the pipe 10 aligned with the opposed window segment 11b is a photosensor 20 which is a photocell or a photodiode as may be found in a commercial unit designated as Eseco Speedmaster, Model Sm 1400 from Eseco of Cushing, Okla.

Connecting the output from the window 11b to the photodiode 20 is a light transmitter 21 which may be a fiber optical bundle. Interposed between the window 11b and the photosensor 20 is a detector filter 22 which preferably is a #92 dichroic filter of wavelength about 620 to about 900 nm. These filters can be eliminated if a light source or filter which generates a single or a band of wavelengths between 550 to 900 nm is used. Its purpose also is to minimize the color effect of the beer from the reading by the photosensor 20.

The output from the photosensor 20 goes to a visual display 23 which may be a digital display for manual or remote monitoring of the turbidity which is read from the stream in the pipe 10.

The output from the photosensor 20 also can be directed to a suitable automatic controller 24 which is used to control a function in the beer processing system. This function can be an automatically controlled valve 25 for directing a stream of beer from a settlement tank to a holding tank for beer waiting to be filtered. It also can be an automatic controller 26 for placing a desired amount of filter aid into a beer suspension being passed through a filter.

Figure 2:
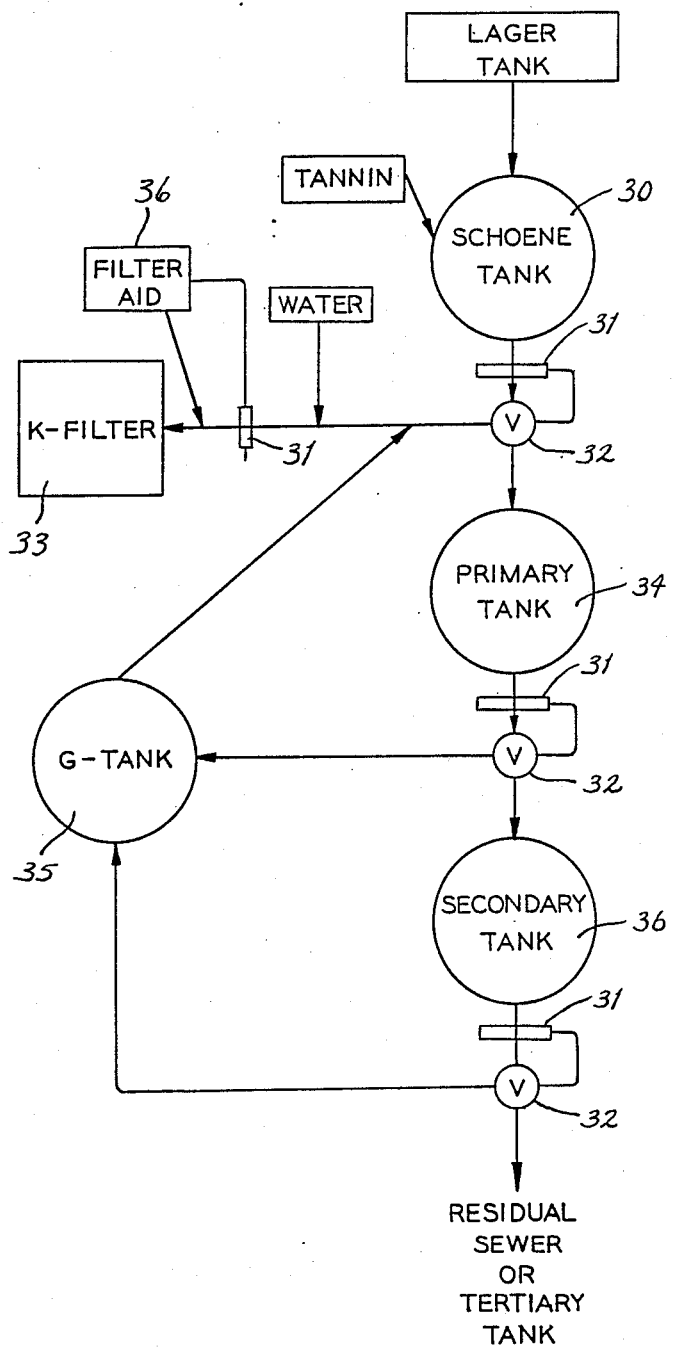
FIG. 2 shows an example of a schematic arrangement of a typical beer production line at the chill-proofing stage and shows the incorporation of the turbidity meters of this invention into such production line.

FIG. 2 shows a typical set up in a beer processing plant. Tannin is added to the beer passing from a larger tank to a Schoene or chill-proofing tank 30. This floculates the protein which settles out. The "clear" beer is decanted from the tank 30 and is monitored by turbidity measuring device 31. The output from the photosensor controls a valve 32 which is programmed to direct the outflow from the tank 30 either to a beer filter 33 or, depending on the turbidity measured, to a primary holding tank 34 where additional sediment is settled out.

The outflow from the primary tank 34 is monitored by another turbidity measuring device 31 which controls a valve 32 which directs said outflow either to a beer holding tank 35 or to a secondary holding tank 36 depending on the turbidity measured.

The outflow from the secondary tank 36 again is monitored by a turbidity measure 31 which controls a valve 32 which directs the outflow to a tertiary tank or to other disposal means or to the beer holding tank 35 depending on the turbidity measured.

The beer from the beer holding tank 35 is piped to the line entering the filter 33. Before going to the filter 33, the turbidity is measured by a turbidity measure 31 which controls a filter aid dispenser 36 where a preselected amount of filter aid is passed to the beer to be filtered depending on its turbidity. This is shown in the following example, Example No. 1.

EXAMPLE NO. 1

Turbidity Measurement of Decanted Beer Prior to Filtration

After the large protein-tannin flocs settle to the bottom of a production tank, the "clear beer" is separated from the sludge. The fine solid particles left in the "clear beer" are removed by filtration. Filter aid is fed to the filtration according to the beer turbidity. The filter life cycle and the finished beer clarity depend greatly on the filter aid feeding rate which in turn is controlled according to beer turbidity. Table 1 shows the turbidity of beer, the amount of filter aid injected in beer filtration per hour and the filter life cycle based on the "clear" beer turbidity and the amount of filter aid to the filtration.

TABLE I

| | Production Beer Filtration | |
|---|---|---|
| Beer Turbidity (PPM) | Filter Aid Feeding Rate (Lbs/Hr) | Filter Life Cycle (Hrs) |
| 64.5 | 210 | 12.4 |
| 90.3 | 293 | 8.9 |
| 129.0 | 419 | 6.2 |
| 167.7 | 545 | 4.8 |

What is claimed is:

1. A device for measuring turbidity of a liquid flowing in a commercial process, which liquid contains an amount of suspended solids, said device comprising:
   (a) a single process line conveying all of the liquid flowing in the commercial process between one region of the process and another region of the process, the flowiing liquid having an amount of suspended solids therein of at least 64.5 ppm up to about 8500 ppm, said process line having a a cross-sectional area sufficient to convey all of the commercial process liquid between the regions so that the fluid depth of flowing commercial process liquid is at least 2 inches up to about 8 inches and having a portion through which the process liquid flows in straight-line fashion without diversion,
   (b) viewing means at the opposite sides of said portion of the process line through which light may enter the process line, be transmitted through the fluid depth of the flowing liquid of the commercial process having suspended solids therein and emerge from the flowing liquid to impinge upon a photosensor means,
   (c) light source means positioned on one side of said process line adjacent to said viewing means for generating light having a wavelength in the range of about 550–900 nm of sufficient intensity as to be transmitted through the fluid depth of the flowing liquid to be detected despite the presence of a maximum amount of 8500 ppm of suspended solids present in the flowing liquid,
   (d) photosensor means optically aligned with the light source means adjacent to the viewing means on the side of the process line opposite to said light source means for picking up and measuring the intensity of light transmitted through the fluid depth of the flowing liquid, and (e) means for controlling the wavelength of the light which is transmitted through the fluid depth of the flowing liquid and is picked up by the photosensor means to a value in the range of about 550–900 nm.

2. The device of claim 1 wherein the means for controlling the light intensity is a power stabilizer means for said light source to provide said light source with a constant voltage.

3. The device of claim 1 including readout means connected to the photosensor for correlating the output to the turbidity of the stream.

4. The device of claim 1 including control means connected to the output of the photosensor means and responsive to said output to control a function acting on the stream.

5. The device of claim 1 wherein the means for controlling the light intensity is filter means between the detector and the stream which passes light of about 550–900 nm in wavelength and which minimizes any color variables in said stream.

6. The device of claim 5 including a second filter between the stream and the light source.

7. The device of claim 1 wherein the means for controlling the light intensity is an internal standard.

8. The device of claim 1 wherein the one region of the process is a Schoene tank and the another region of the process is a beer filter process, and including means responsive to the turbidity measured by the photosensor means for controlling introduction of filter aid into the beer filter process.

9. A process for measuring a broad range of turbidity in a flowing liquid stream in a commercial process line including the steps of:

(a) providing a single commercial process line having viewing means at opposite sides of the transverse depth thereof through which light may enter the process line, be transmitted through the flowing liquid stream and emerge from the process line, (b) passing a flowing liquid stream of process liquid through the single process line between one region of the process and another region of the process, the single process line having a straight-through portion passing the flowing liquid stream and having a cross-sectional area sufficient to convey all of the flowing stream so that the fluid depth of the flowing stream is at least 2 inches up to about 8 inches in depth and containing an amount of suspended solids of at least 64.5 ppm up to about 8500 ppm in the process line past the viewing means, (c) directing light having a wavelength in the range of about 550–900 nm through the viewing means and said transverse depth of the flowing stream of liquid, said light having sufficient intensity to be transmitted through the depth of flowing liquid and be detected despite the presence of 8500 ppm suspended solids in the flowing liquid stream, (d) detecting and measuring the intensity of light having a wavelength in the range of about 550–900 nm transmitted through the depth of the flowing liquid stream, and (e) converting the intensity of transmitted light having a wavelength in the range of about 550–900 nm measured in step (d) into a value indicative of the turbidity of said flowing liquid stream.

10. The process of claim 9 including the step of correcting the intensity of the light by comparing the output to an internal standard to minimize light intensity effect due to power fluctuation.

11. The process of claim 9 including the step of digitally displaying the turbidity.

12. The process of claim 9 including the step of directing the output from said light measure to control means for another function to be applied to said stream.

13. The process of claim 9 including the step of stabilizing the power source to minimize the light intensity effect due to power fluctuation.

14. A method of measuring turbidity in a dynamic stream in a beer processing plant after sedimentation of the beer, comprising the steps of:

(a) measuring the turbidity of a stream of chill-proofed beer containing at least 64.5 ppm up to 8500 ppm solids in a single processing line leading from a sedimentation tank, the processing line having a straight through portion of cross-sectional area sufficient to convey all of the chill-proofed beer leading from the sedimentation tank so that the fluid depth of chill-proofed beer in the straight through portion is at least 2 inches up to 8 inches, (b) directing the stream of chill-proofed beer to a settling tank or a beer filter process depending on the turbidity measured in stap (a), the chill-proofed beer directed to the beer filter process flowing in a further single process line having a straight through portion of cross-sectional area sufficient to convey all of the chill-proofed beer directed to the beer filter process so that the fluid depth of the chill-proofed beer directed to the beer filter process is at least 2 inches up to 8 inches, (c) measuring the turbidity of beer in the straight through portion of the further process line before entering the beer filter process, and (d) adding filter aid to the beer filter process and controlling the amount of filter aid added to the beer filter process depending on the turbidity measured in step (c).

15. The method of claim 14 including the step of continuously measuring the turbidity of the beer entering the filtration and continuously changing the rate of feed of filter aid to the filtration process during the filtration in response to changes in turbidity.

16. The method of claim 14 wherein the turbidity is measured by directing a steady stream of light having a wavelength of about 550–900 nm across said stream and picking up said light on the opposite side of said stream.

17. The method of claim 16 wherein the turbidity is measured by directing a steady stream of light from a quartz halogen lamp across said stream and filtering said light dichromically to remove variations in the transmitted light due to colors present in the beer.

* * * * *